United States Patent
Ushida et al.

(10) Patent No.: US 11,931,535 B2
(45) Date of Patent: Mar. 19, 2024

(54) GUIDE WIRE

(71) Applicant: ASAHI INTECC CO., LTD., Seto (JP)

(72) Inventors: Keisuke Ushida, Seto (JP); Naozumi Iwata, Seto (JP)

(73) Assignee: ASAHI INTECC CO., LTD., Seto (JP)

( * ) Notice: Subject to any disclaimer, the term of this patent is extended or adjusted under 35 U.S.C. 154(b) by 698 days.

(21) Appl. No.: 17/118,730

(22) Filed: Dec. 11, 2020

(65) Prior Publication Data

US 2021/0093838 A1  Apr. 1, 2021

Related U.S. Application Data

(63) Continuation of application No. PCT/JP2018/024867, filed on Jun. 29, 2018.

(51) Int. Cl.
*A61M 25/09* (2006.01)

(52) U.S. Cl.
CPC ... *A61M 25/09* (2013.01); *A61M 2025/09091* (2013.01)

(58) Field of Classification Search
CPC ........ A61M 25/09; A61M 2025/09091; A61M 25/0041; A61M 2025/09083; A61M 2025/09175; A61M 2025/09058; A61B 5/6851
See application file for complete search history.

(56) References Cited

U.S. PATENT DOCUMENTS

| | | | |
|---|---|---|---|
| 4,958,642 A | 9/1990 | Christian et al. | |
| 5,147,317 A | 9/1992 | Shank et al. | |
| 5,797,857 A | 8/1998 | Obitsu | |
| 2002/0010426 A1 | 1/2002 | Clayman et al. | |
| 2003/0181827 A1 | 9/2003 | Hojeibane et al. | |
| 2010/0318001 A1* | 12/2010 | Miyata | A61B 17/17 600/585 |
| 2013/0172782 A1 | 7/2013 | Hilmersson | |
| 2013/0289445 A1 | 10/2013 | Edamatsu | |

FOREIGN PATENT DOCUMENTS

| | | |
|---|---|---|
| JP | H02-199781 A | 8/1990 |
| JP | 2004-533271 A | 11/2004 |
| JP | 2007-075531 A | 3/2007 |
| JP | 2011-000199 A | 1/2011 |
| JP | 2013-226301 A | 11/2013 |
| JP | 2015-062442 A | 4/2015 |
| JP | 2015-89379 A | 5/2015 |
| JP | 2018-027221 A | 2/2018 |
| WO | 02/28467 A1 | 4/2002 |

* cited by examiner

*Primary Examiner* — Jason E Flick (74) *Attorney, Agent, or Firm* — Oliff PLC (57) ABSTRACT

A guide wire includes a core shaft, a coil body curved from the proximal end side to the distal end side of the guide wire, and a fixing portion fixing the core shaft to the coil body. The core shaft includes a first contact part in contact with an inner surface of the coil body on an opposite side to the curving direction, and a second contact part in contact with the inner surface of the coil body in the curving direction, at a position closer to the distal end than the first contact part. The fixing portion includes a first fixing portion fixing the core shaft to the coil body at a position closer to the proximal end than the first contact part, and a second fixing portion fixing the core shaft to the coil body at a position closer to the distal end than the second contact part.

12 Claims, 11 Drawing Sheets

GUIDE WIRE

CROSS REFERENCE TO RELATED APPLICATION

This is a Continuation of PCT/JP2018/024867 filed Jun. 29, 2018. The disclosure of the prior application is hereby incorporated by reference herein in its entirety.

TECHNICAL FIELD

Disclosed embodiments relate to a guide wire.

BACKGROUND

There is known a guide wire used for inserting a catheter or the like into a blood vessel. In such a guide wire, to improve vascular selectivity and guide the guide wire smoothly to a target site in the blood vessel, the distal end portion of the guide wire may be shaped in a small curve or the like. For example, Patent Literature 1 discloses a guide wire in which a distal end part of a core shaft (core wire) is provided with a plate-like plate-shaped part to facilitate shaping of the distal end portion of the guide wire. Patent Literature 2 discloses a guide wire having improved operability by including a flexible curved part on a core shaft (core member). Patent Literature 3 discloses a guide wire which has a core shaft (core wire) including a sleeve and a conductive material and has an electric function.

A guide wire made of a metal coil generally includes a core shaft as described above and a coil body formed by winding a wire around the core shaft. Patent Literature 2 describes the core shaft fixed to the coil body in a state where the core shaft and the coil body (tubular member) are axially displaced. This makes it possible to maintain a shape imparted to the guide wire. However, in the guide wire described in Patent Literature 2, the rigidity of the coil body is low, and thus there is a problem that the shape imparted to the guide wire is easily lost especially if a load is applied to the shaped portion. Further, as to guide wires described in Patent Literatures 1 and 3, there is no description about maintaining the shape imparted to the guide wire. Such a problem is not limited to the vascular system, and is common to a guide wire to be inserted into various organs of a human body, such as the lymphatic system, the biliary system, the urinary system, the respiratory system, the digestive system, the secretory gland, and the reproductive organs.

CITATION LIST

Patent Literature 1: Japanese Unexamined Patent Application Publication No. 2018-27221
Patent Literature 2: Japanese Unexamined Patent Application Publication (Translation of PCT Application) No. 2004-533271
Patent Literature 3: Japanese Unexamined Patent Application Publication No. 1102-199781

SUMMARY

The disclosed embodiments have been devised to address the above-described problems, and an object thereof is to provide a guide wire in which the distal end portion can be easily shaped and maintainability of the imparted shape can be improved.

The disclosed embodiments include the following aspects.

(1) According to one aspect of the disclosed embodiments, a guide wire is provided. The guide wire includes a core shaft, a coil body formed by winding a wire around the core shaft and curved from the proximal end side to the distal end side of the guide wire, and a fixing portion fixing the core shaft to the coil body. The core shaft includes a first contact part in contact with an inner surface of the coil body on an opposite side to the curving direction, and a second contact part in contact with the inner surface of the coil body in the curving direction, at a position closer to the distal end than the first contact part. The fixing portion includes a first fixing portion fixing the core shaft to the coil body at a position closer to the proximal end than the first contact part, and a second fixing portion fixing the core shaft to the coil body at a position closer to the distal end than the second contact part.

According to this configuration, the core shaft is fixed to the coil body at two points, i.e., the first fixing portion on the proximal end side and the second fixing portion on the distal end side, in a state where the core shaft is in contact with the inner surface of the coil body on the opposite side to the curving direction, at the first contact part, and is in contact with the inner surface of the coil body in the curving direction, at the second contact part closer to the distal end than the first contact part. Therefore, even if a force is applied to the guide wire in a direction such that the curvature of the curved coil body is decreased, the curvature of the coil body can be maintained. This is because the core shaft is supported at the two points, i.e., the second fixing portion and the first contact part, and thus in response to the applied force, a tensile force can be applied to the core shaft. Further, if a force is applied to the guide wire in a direction such that the curvature of the curved coil body is increased, a bending force can be applied from the coil body to the core shaft by using the second contact part as a fulcrum, and thus further shaping of the coil body can be easily performed. As a result, according to this configuration, it is possible to provide a guide wire in which the distal end portion can be easily shaped and the maintainability of the imparted shape can be improved.

(2) In the guide wire according to the above-described aspect, the second fixing portion may fix a distal end part of the core shaft to a distal end part of the coil body. According to this configuration, the second fixing portion fixes the distal end part of the core shaft to the distal end part of the coil body, and thus it is possible to prevent an inner wall of a blood vessel or the like from being damaged by an exposed distal end part of the core shaft or the coil body.

(3) The guide wire according to the above-described aspect may further include an outer coil body formed by winding a wire around the coil body and curved in the curving direction of the coil body. According to this configuration, the outer coil body formed around the coil body facilitates transmission of an operation on the guide wire performed at a portion held in the operator's hand, to the distal end portion. As a result, the torquability of the guide wire can be improved.

(4) The guide wire according to the above-described aspect may further include a distal tip fixing a distal end part of the outer coil body to the distal end part of the core shaft. According to this configuration, the distal tip fixes the distal end part of the outer coil body to the distal end part of the core shaft, and thus even in the configuration including the outer coil body, the distal end portion can be easily shaped and the maintainability of the imparted shape can be improved.

(5) In the guide wire according to the above-described aspect, the first fixing portion may fix the core shaft to a proximal end part of the coil body. According to this configuration, the first fixing portion fixes the core shaft to the proximal end part of the coil body, and thus it is possible to easily design the structure of each portion of the guide wire.

The disclosed embodiments can be implemented in various aspects including, for example, a method of manufacturing a guide wire.

DETAILED DESCRIPTION OF EMBODIMENTS ON

First Embodiment

Figure 1:
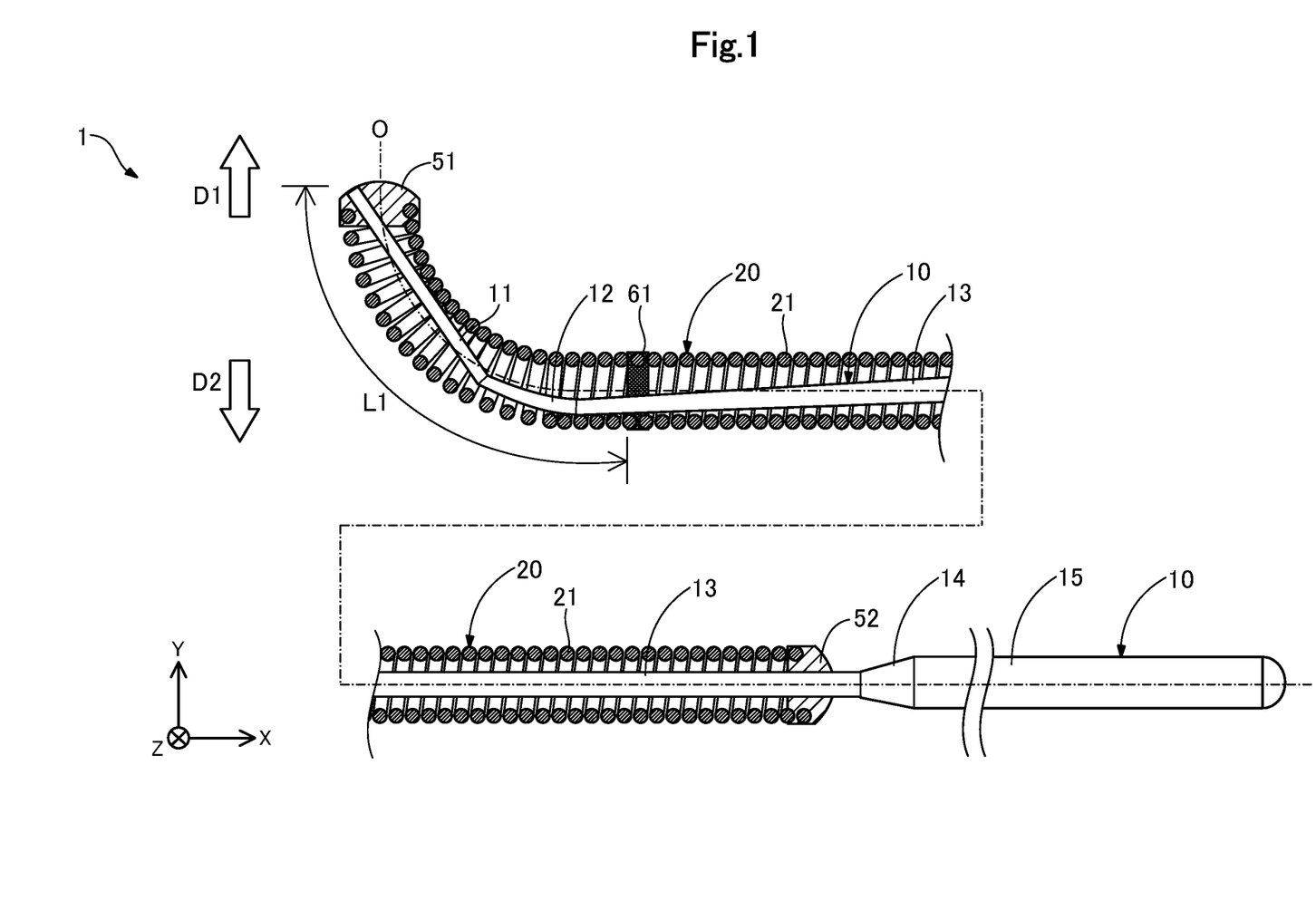
FIG. 1 is a partial cross-sectional view illustrating an overall configuration of a guide wire according to a first embodiment.

FIG. 1 is a partial cross-sectional view illustrating an overall configuration of a guide wire 1 according to a first embodiment. The guide wire 1 is a medical device used when a catheter is inserted into, for example, a blood vessel, and includes a core shaft 10, a coil body 20, a distal end side fixing portion 51, a proximal end side fixing portion 52, and an intermediate fixing portion 61. In FIG. 1, an axis passing through the center of the guide wire 1 is represented by an axis O (dot and dash line). In the following examples, axes passing through the centers of a third reduced-diameter part 14 and a large-diameter part 15 in the core shaft 10, and an axis passing through the center of the coil body 20 all coincide with the axis O. On the other hand, axes passing through the centers of a small-diameter part 11, a first reduced-diameter part 12, and a second reduced-diameter part 13 of the core shaft 10 do not coincide with the axis O. The axes passing through the centers of the third reduced-diameter part 14 and the large-diameter part 15 and the axis passing through the center of the coil body 20 each may not coincide with the axis O.

In FIG. 1, an X-axis, Y-axis, and Z-axis that are orthogonal to each other are illustrated. The X-axis corresponds to the axial direction of the guide wire 1, the Y-axis corresponds to the height direction of the guide wire 1, and the Z-axis corresponds to the width direction of the guide wire 1. The left side (−X-axis direction) in FIG. 1 is referred to as "distal end side" of the guide wire 1 and components, and the right side in FIG. 1 (+X-axis direction) is referred to as a "proximal end side" of the guide wire 1 and components. Further, with respect to the guide wire 1 and components, an end part located on the distal end side is referred to as a "distal end part" or simply a "distal end," and an end part located on the proximal end side is referred to as a "proximal end part" or simply a "proximal end". In the present embodiment, the distal end side corresponds to a "distal side," and the proximal end side corresponds to a "proximal side." These are also true for any other drawings following FIG. 1 illustrating overall configurations.

As illustrated in FIG. 1, a portion of the guide wire 1 on the distal end side has a curved shape (bent shape) that is curved (bent) in the +Y-axis direction from the proximal end side to the distal end side. Hereinafter, the curving direction of the guide wire 1 (+Y-axis direction) is also referred to as "curving direction D1", and the direction opposite to the curving direction (−Y-axis direction) is also referred to as "opposite direction D2" (white arrows D1 and D2 in FIG. 1).

The core shaft 10 is a tapered long member having a large diameter at the proximal end side and a small diameter at the distal end side. The core shaft 10 can be formed of a material such as a stainless steel alloy including SUS304, SUS316, etc., a superelastic alloy including a nickel-titanium (NiTi) alloy, etc., a piano wire, a nickel-chromium base alloy, a cobalt alloy, or tungsten. The core shaft 10 may be formed of a known material other than the above. The core shaft 10 includes the small-diameter part 11, the first reduced-diameter part 12, the second reduced-diameter part 13, the third reduced-diameter part 14, and the large-diameter part 15, in this order from the distal end side to the proximal end side. The outer diameter and length of each part can be arbitrarily set.

The small-diameter part 11 is positioned at the distal end part of the core shaft 10. The small-diameter part 11 is a part where the outer diameter of the core shaft 10 is smallest, and has a substantially columnar (cylindrical) shape having a constant outer diameter. The small-diameter part 11 of the present embodiment is not curved and has a linear shape, and is arranged inside the coil body 20 and in a state of being inclined (angled) in the curving direction D1, from the proximal end side to the distal end side.

The first reduced-diameter part 12 is positioned between the small-diameter part 11 and the second reduced-diameter part 13. The first reduced-diameter part 12 slightly decreases in outer diameter from the proximal end side toward the distal end side to form a substantially frustoconical shape. To the first reduced-diameter part 12 of the present embodiment, a curved shape (bent shape) that is curved (bent) in the curving direction D1 is imparted. The first reduced-diameter part 12 is arranged inside the coil body 20 and in a state of being inclined in the curving direction D1, from the proximal end side to the distal end side. In the illustrated example, the inclination angle of the first reduced-diameter part 12 in the curving direction D1 is smaller than the inclination angle of the small-diameter part 11 in the curving direction D1, with respect to the axis O.

The second reduced-diameter part 13 is positioned between the first reduced-diameter part 12 and the third reduced-diameter part 14. The second reduced-diameter part 13 slightly decreases in outer diameter from the proximal end side toward the distal end side to form a substantially frustoconical shape. The second reduced-diameter part 13 of the present embodiment is not curved and has a linear shape, and is arranged inside the coil body 20 and in a state of being inclined in the opposite direction to the curving direction D1 (i.e., in the opposite direction D2), from the proximal end side to the distal end side.

The third reduced-diameter part 14 is positioned between the second reduced-diameter part 13 and the large-diameter part 15. The third reduced-diameter part 14 decreases in outer diameter from the proximal end side toward the distal end side to form a substantially frustoconical shape. The large-diameter part 15 is positioned at the proximal end part of the core shaft 10. The large-diameter part 15 has a substantially columnar shape having a constant outer diameter larger than the outer diameter of the small-diameter part 11. The outer surfaces of the small-diameter part 11, the first reduced-diameter part 12, and the second reduced-diameter part 13 are covered by the coil body 20 described below. On the other hand, the third reduced-diameter part 14 and the large-diameter part 15 are not covered by the coil body 20 and are exposed from the coil body 20. An operator uses the large-diameter part 15 to grip the guide wire 1.

The coil body 20 has a substantially hollow cylindrical shape formed by spirally winding a wire 21 around the core shaft 10. A portion of the coil body 20 on the distal end side has a curved shape (bent shape) that is curved (bent) in the curving direction D1 from the proximal end side to the distal end side. The wire 21 forming the coil body 20 may be a solid wire that is a single wire or a stranded obtained by twisting a plurality of wires. If the wire 21 is a solid wire, the coil body 20 is configured as a single coil, and if the wire 21 is a stranded wire, the coil body 20 is configured as a hollow stranded coil. Further, the coil body 20 may be configured by combining a single coil and a hollow stranded coil. To facilitate imparting a curved shape to the coil body 20, it is preferable that at least a portion of the coil body 20 on the distal end side is a hollow stranded coil. The wire diameter of the wire 21 and the average coil diameter in the coil body 20 (an average diameter of outer and inner diameters of the coil body 20) can be arbitrarily set.

The wire 21 can be formed of, for example, a stainless steel alloy such as SUS304, SUS316, etc., a superelastic alloy such as a Ni—Ti alloy, a piano wire, a radiolucent alloy such as a nickel-chromium base alloy, a cobalt alloy, etc., gold, platinum, tungsten, and a radiopaque alloy such as an alloy containing these elements (for example, a platinum-nickel alloy). The wire 21 may be formed of a known material other than the above materials.

The distal end side fixing portion 51 is positioned at the distal end part of the guide wire 1 and integrally holds (directly joins) the distal end part of the small-diameter part 11 of the core shaft 10 and the distal end part of the coil body 20. The distal end side fixing portion 51 can be formed of any bonding agent, for example, a metal solder such as silver solder, gold solder, zinc, Sn—Ag alloy, Au—Sn alloy, etc., or an adhesive such as an epoxy adhesive. The proximal end side fixing portion 52 is positioned at the proximal end part of the second reduced-diameter part 13 of the core shaft 10, and integrally holds the core shaft 10 and the proximal end part of the coil body 20. The proximal end side fixing portion 52 can be formed of any bonding agent, similarly to the distal end side fixing portion 51. A bonding agent used for the proximal end side fixing portion 52 and a bonding agent used for the distal end side fixing portion 51 may be the same or different.

The intermediate fixing portion 61 integrally holds the coil body 20 and the core shaft 10 at or near an intermediate portion of the coil body 20 in the axis O direction (X-axis direction). The intermediate fixing portion 61 can be formed of any bonding agent, similarly to the distal end side fixing portion 51. A bonding agent used for the intermediate fixing portion 61 and a bonding agent used for the distal end side fixing portion 51 may be the same or different. Although the one intermediate fixing portion 61 is illustrated in FIG. 1, the guide wire 1 may be provided with a plurality of intermediate fixing portions 61.

Figure 2:
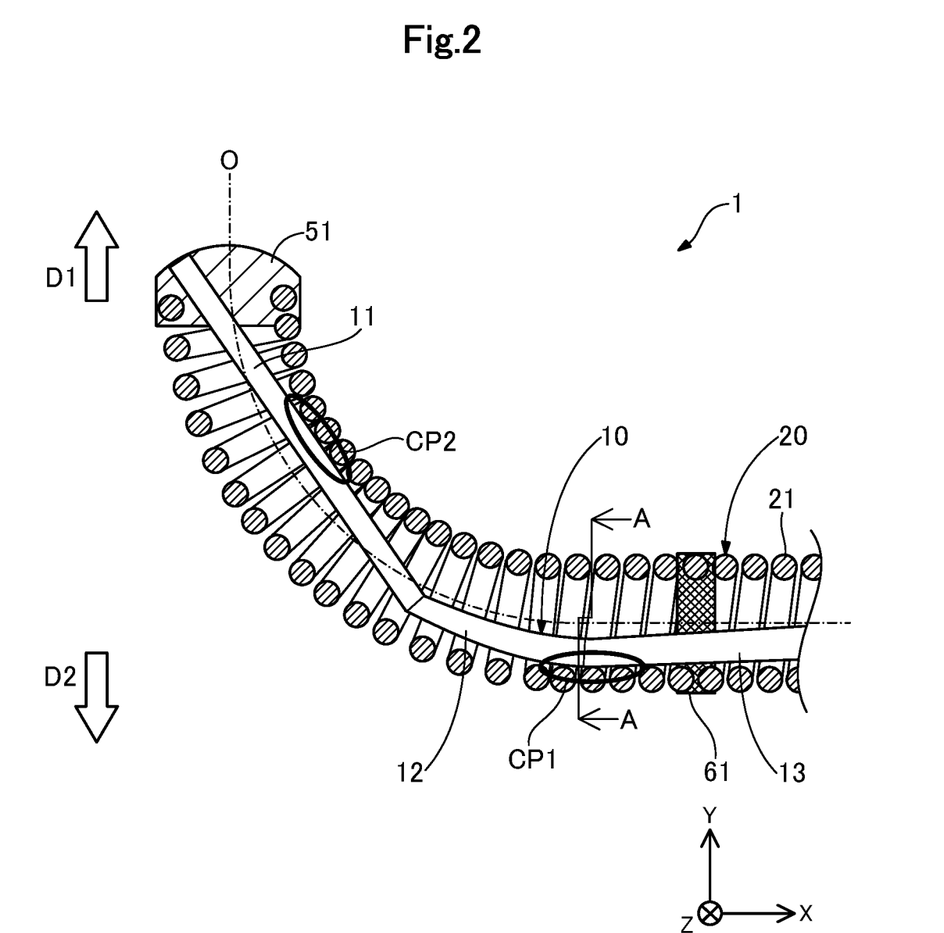
FIG. 2 is a partial cross-sectional view of a distal end side of the guide wire.
Figure 3:
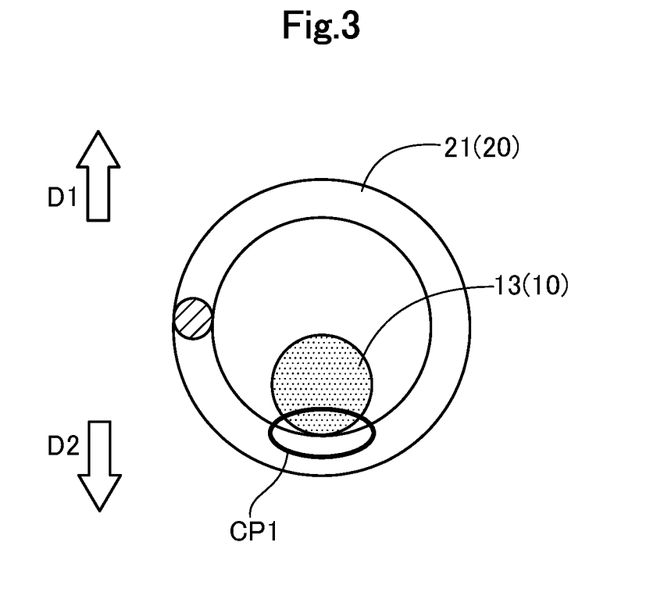
FIG. 3 is a cross-sectional view of the guide wire taken along a line A-A (FIG. 2).

FIG. 2 is a partial cross-sectional view of the distal end side of the guide wire 1. FIG. 3 is a cross-sectional view of the guide wire 1 taken along a line A-A (FIG. 2). The X-axis, Y-axis, and Z-axis illustrated in FIG. 2 correspond to the X-axis, Y-axis, and Z-axis in FIG. 1, respectively. This is also true for any other drawings following FIG. 2 which include the X-axis, Y-axis, and Z-axis.

As illustrated in FIGS. 2 and 3, the core shaft 10 has a "first contact part CP1" that is in contact with the inner surface of the coil body 20 on the opposite side to the curving direction D1 (opposite direction D2). In the example of FIG. 2, the first contact part CP1 is provided at the boundary between the proximal end part of the first reduced-diameter part 12 and the distal end part of the second reduced-diameter part 13. However, the first contact part CP1 may be provided at any position such as the middle portion of the first reduced-diameter part 12 or a portion of the second reduced-diameter part 13 on the distal end side. Further, as illustrated in FIG. 2, the core shaft 10 has a "second contact part CP2" that is in contact with the inner surface of the coil body 20 in the curving direction D1, at a position closer to the distal end of the guide wire 1 than the first contact part CP1. In the example of FIG. 2, the second contact part CP2 is provided at a substantially middle portion of the small-diameter part 11. However, the second contact part CP2 may be provided at any position such as a portion of the small-diameter part 11 on the distal end side or the proximal end side or a portion of the first reduced-diameter part 12.

As a result of having the first contact part CP1 and the second contact part CP2 on the distal end side of the core shaft 10, the axis passing through the center of the core shaft 10 does not coincide with the axis O of the guide wire 1 and the coil body 20.

As illustrated in FIG. 2, the intermediate fixing portion 61 is positioned closer to the proximal end of the guide wire 1 than the first contact part CP1. The intermediate fixing portion 61 fixes a portion of the second reduced-diameter part 13 arranged in a state of being inclined in the opposite direction D2 in order to maintain a contact state between the core shaft 10 and the coil body 20 at the first contact part CP1. The intermediate fixing portion 61 functions as a "first fixing portion". In addition, the distal end side fixing portion 51 is positioned closer to the distal end of the guide wire 1 than the second contact part CP2, and fixes a portion (the distal end part in the illustrated example) of the small-diameter part 11 arranged in a state of being inclined in the curving direction D1 in order to maintain a contact state between the core shaft 10 and the coil body 20 at the second contact part CP2. The distal end side fixing portion 51 functions as a "second fixing portion".

The intermediate fixing portion 61 (first fixing portion) and the distal end side fixing portion 51 (second fixing portion) are also collectively referred to as "fixing portions". In the guide wire 1 of the present embodiment, the contact states between the core shaft 10 and the coil body 20 at the first contact part CP1 and the second contact part CP2 are maintained by these two fixing portions. A length L1 (FIG. 1) from the distal end part of the distal end side fixing portion 51 to the distal end part of the intermediate fixing portion 61 may be any length and may be set depending on, for example, the length of a portion where shaping to the guide wire 1 is supposed to be performed.

Figure 4:
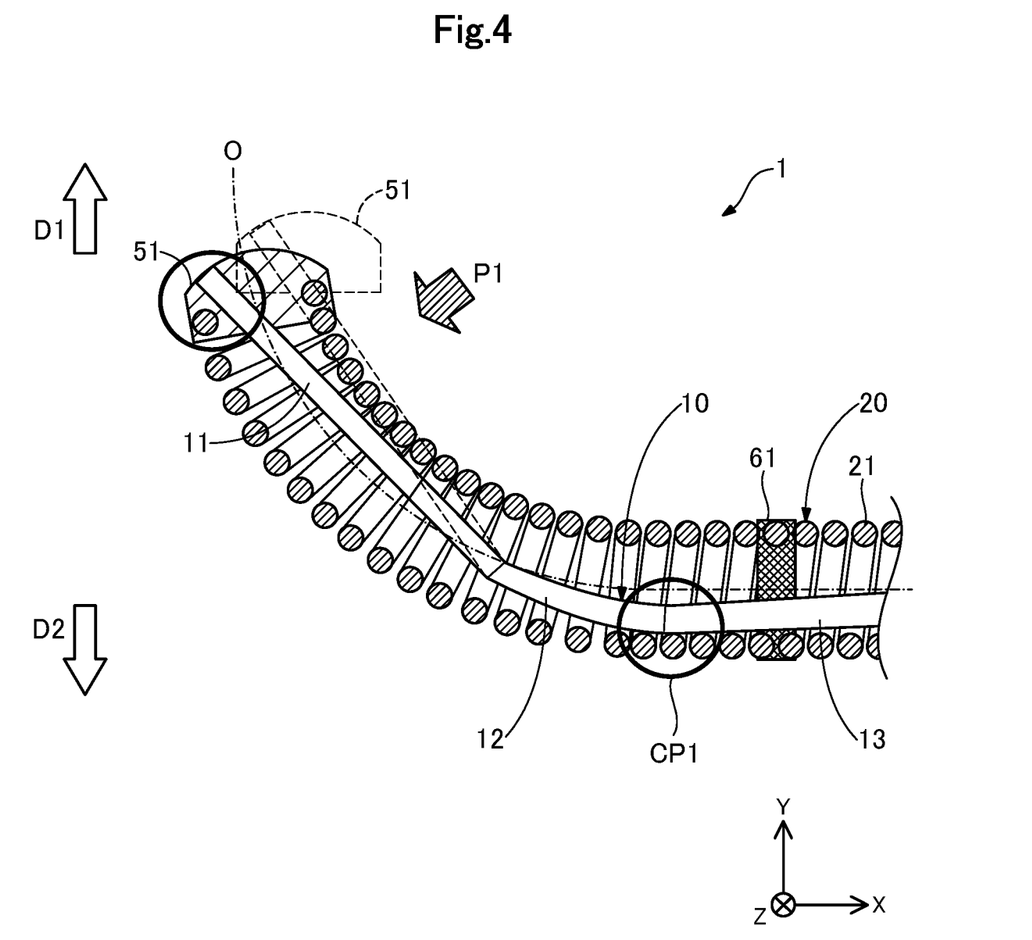
FIG. 4 is a diagram illustrating an example of the guide wire during use.

FIG. 4 is a diagram illustrating an example of the guide wire 1 during use. As described above, in the guide wire 1 of the present embodiment, the core shaft 10 is fixed to the coil body 20 at two points, i.e., the intermediate fixing portion 61 (first fixing portion) on the proximal end side and the distal end side fixing portion 51 (second fixing portion) on the distal end side in a state where the core shaft 10 is in contact with the inner surface of the coil body 20 on the opposite side (opposite direction D2) to the curving direction D1 at the first contact part CP1, and is in contact with the inner surface of the coil body 20 in the curving direction D1 at the second contact part CP2 closer to the distal end of the guide wire 1 than the first contact part CP1. If a force P1 is applied to the distal end side of the guide wire 1 in a direction (an arrow hatched with oblique lines in FIG. 4) such that the curvature of the curved coil body 20 is decreased, the distal end side of the guide wire 1 slightly moves, due to the action of the force P1, from the original position (represented by a broken line in FIG. 4) in the direction of the force P1 (as represented by a solid line in FIG. 4). However, in the guide wire 1 of the present embodiment, the core shaft 10 is supported at the two points (circles in FIG. 4), i.e., the distal end side fixing portion 51 (second fixing portion) and the first contact part CP1, and thus a tensile force can be applied to the core shaft 10 in response to the force P1. Thus, the curvature of the coil body 20 can be maintained as compared with a conventional configuration without the first contact part CP1.

Figure 5:
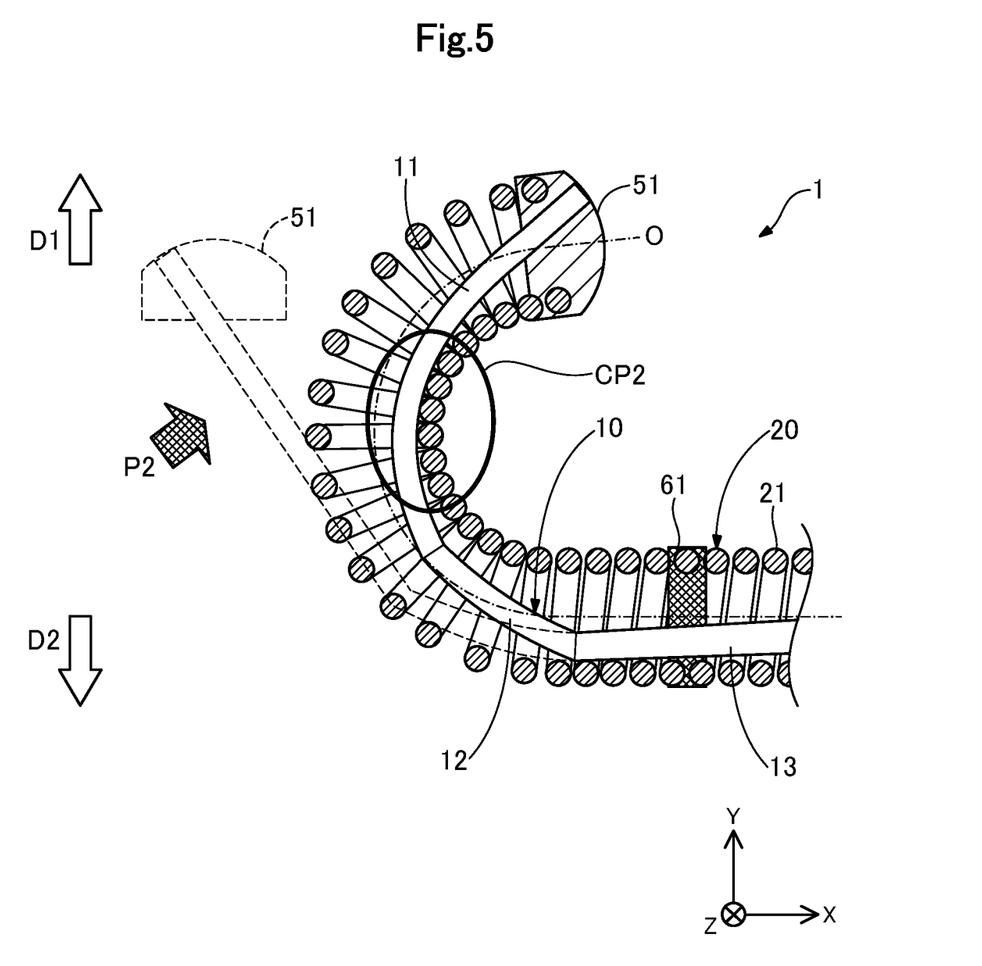
FIG. 5 is a diagram illustrating another example of the guide wire during use.

FIG. 5 is a diagram illustrating another example of the guide wire 1 during use. If a force P2 is applied to the distal end side of the guide wire 1 in a direction (a cross-hatched arrow in FIG. 5) such that the curvature of the curved coil body 20 is increased, the distal end side of the guide wire 1 moves, due to the action of the force P2, from the original position (represented by a broken line in FIG. 5) in the direction of the force P2 (as represented by a solid line in FIG. 5). At this time, a bending force can be applied from the coil body 20 to the core shaft 10 by using the second contact part CP2 as a fulcrum (a circle in FIG. 5), and thus further shaping of the coil body 20 can be performed more easily as compared with a conventional configuration without the second contact part CP2. As a result, according to the guide wire 1 of the present embodiment, it is possible to provide the guide wire 1 in which the distal end portion can be easily shaped and the maintainability of the imparted shape can be improved.

Further, in the guide wire 1 of the present embodiment, the distal end side fixing portion 51 (second fixing portion) fixes the distal end part of the core shaft 10 to the distal end part of the coil body 20, and thus as compared with the configuration in which the distal end part of the core shaft 10 or the distal end part of the coil body 20 is exposed, it is possible to prevent an inner wall of a blood vessel or the like from being damaged by such an distal end part.

Second Embodiment

Figure 6:
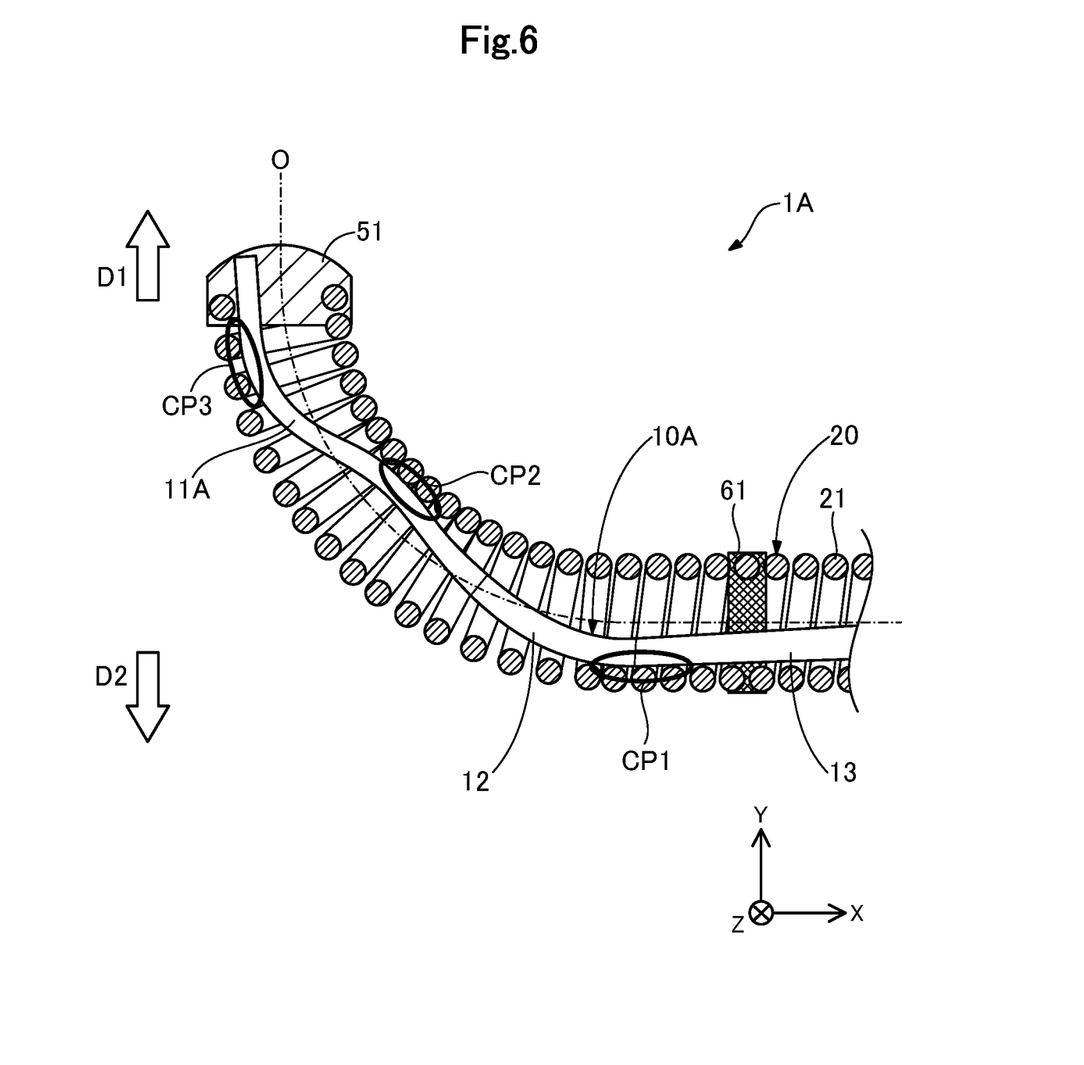
FIG. 6 is a partial cross-sectional view of a distal end side of a guide wire according to a second embodiment.

FIG. 6 is a partial cross-sectional view of a distal end side of a guide wire 1A according to a second embodiment. The guide wire 1A of the second embodiment further includes a "third contact part CP3" at a position closer to the distal end of the guide wire 1A than the second contact part CP2. In the third contact part CP3, a core shaft 10A is in contact with the inner surface of the coil body 20 on the opposite side to the curving direction D1 (opposite direction D2). Specifically, the core shaft 10A includes a curved small-diameter part 11A instead of the linear small-diameter part 11. From the proximal end side to the distal end side, the small-diameter part 11A has a curved shape (bent shape) which is first curved (bent) in the curving direction D1, and then curved in the opposite direction D2. In the small-diameter part 11A, the curvature in the curving direction D1 forms the second contact part CP2, and the curvature in the opposite direction D2 forms the third contact part CP3.

The guide wire 1A according to the second embodiment can also exhibit a similar effect to the first embodiment. In the second embodiment, the case where the core shaft 10A forms three contact parts that alternately come into contact with the inner surface of the coil body 20 in the opposite direction D2 and the inner surface of the coil body 20 in the curving direction D1 is illustrated. However, the core shaft 10A may have four or more contact parts that alternately come into contact with the inner surfaces of the coil body 20.

Third Embodiment

Figure 7:
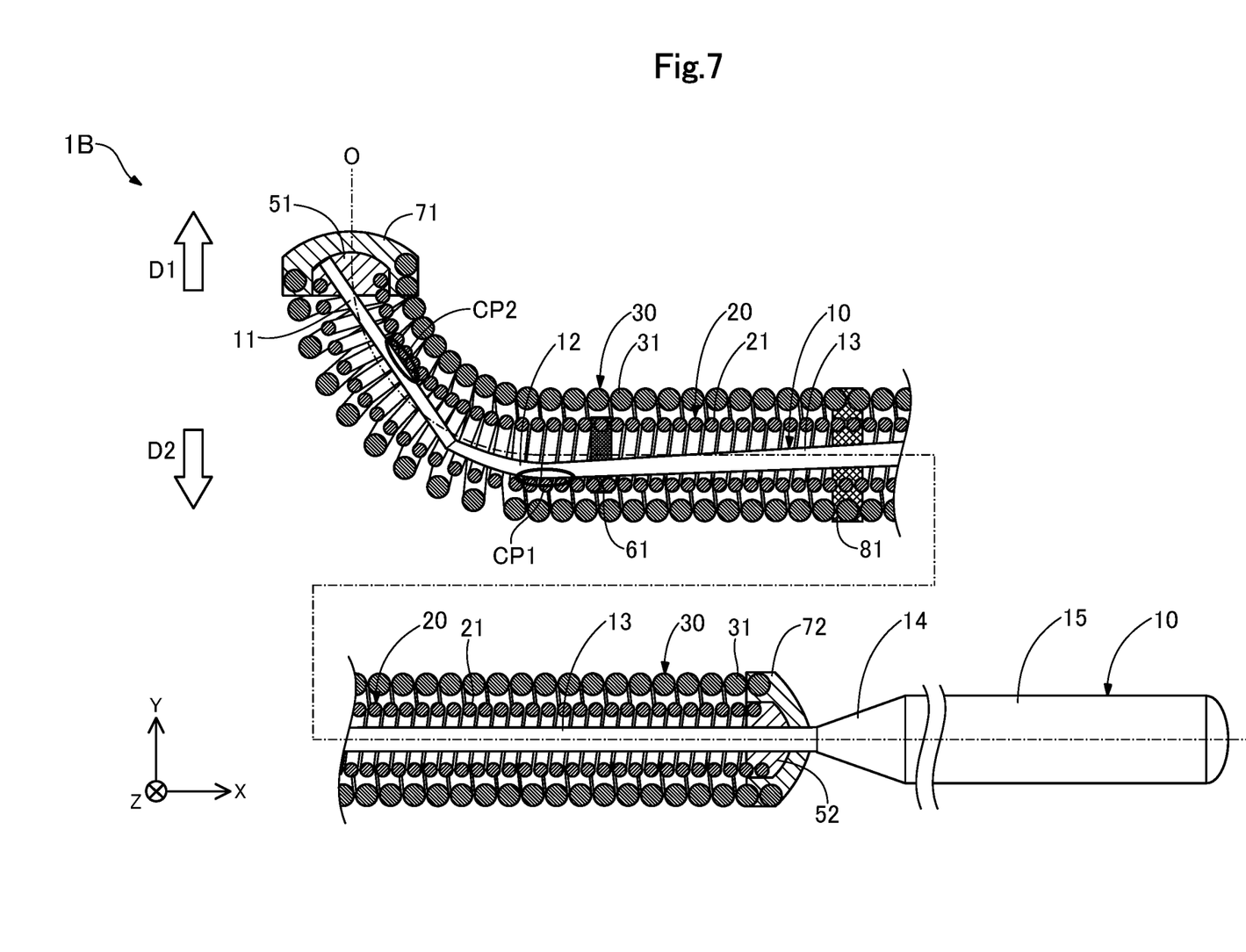
FIG. 7 is a partial cross-sectional view illustrating an overall configuration of a guide wire according to a third embodiment.

FIG. 7 is a partial cross-sectional view illustrating an overall configuration of a guide wire 1B according to a third embodiment. The guide wire 1B of the third embodiment further includes an outer coil body 30 that covers the outside of the coil body 20. In the illustrated example, the axis passing through the center of the outer coil body 30 coincides with the axis O. However, the axis passing through the center of the outer coil body 30 may not coincide with the axis O. The outer coil body 30 has a substantially hollow cylindrical shape formed by spirally winding a wire 31 around the coil body 20. Similarly to the coil body 20, a portion of the outer coil body 30 on the distal end side has a curved shape (bent shape) that is curved (bent) in the curving direction D1 from the proximal end side to the distal end side. The inner diameter of the outer coil body 30 is larger than the outer diameter of the coil body 20, and the winding direction of the wire 31 is opposite to the winding direction of the coil body 20. However, the winding direction of the wire 31 in the outer coil body 30 may be the same as that in the coil body 20, or may be a different direction other than the opposite direction. As with the wire 21, the wire 31 may be a solid wire or a stranded wire. Alternatively, the outer coil body 30 may be configured by combining a single coil formed of a solid wire and a hollow stranded coil formed of a stranded wire. The wire 31 having any diameter can be used. The wire 31 can be formed of the same material as the wire 21. The material used for the wire 31 may be the same as or different from that used for the wire 21.

The guide wire 1B of the third embodiment further includes a distal tip 71, a proximal tip 72, and a second intermediate fixing portion 81. The distal tip 71 is positioned at the distal end part of the guide wire 1B, and integrally holds the distal end part of the outer coil body 30 and the distal end side fixing portion 51. The proximal tip 72 is positioned at the proximal end part of the second reduced-diameter part 13 of the core shaft 10, and integrally holds the proximal end part of the outer coil body 30 and the proximal end side fixing portion 52. The second intermediate fixing portion 81 is provided closer to the proximal end of the guide wire 1B than the intermediate fixing portion 61, and integrally holds a portion of the core shaft 10, a portion of the coil body 20, and a portion of the outer coil body 30. The distal tip 71, the proximal tip 72, and the second intermediate fixing portion 81 each can be formed of any bonding agent, similarly to the distal end side fixing portion 51. Bonding agents used for the distal tip 71, the proximal tip 72, the second intermediate fixing portion 81, and the distal end side fixing portion 51 may be the same or different.

The guide wire 1B according to the third embodiment can also exhibit a similar effect to the first embodiment. According to the guide wire 1B of the third embodiment, the outer coil body 30 formed around the coil body 20 facilitates transmission of an operation on the guide wire 1B performed at a portion held in the operator's hand (the large-diameter part 15 of the core shaft 10), to the distal end portion of the guide wire 1B. As a result, the torquability of the guide wire 1B can be improved. Furthermore, the guide wire 1B of the third embodiment includes the distal tip 71 that fixes the distal end part of the outer coil body 30 to the distal end side fixing portion 51, and thus even in the configuration including the outer coil body 30, the distal end portion of the guide wire 1B can be easily shaped and the maintainability of the imparted shape can be improved.

Fourth Embodiment

Figure 8:
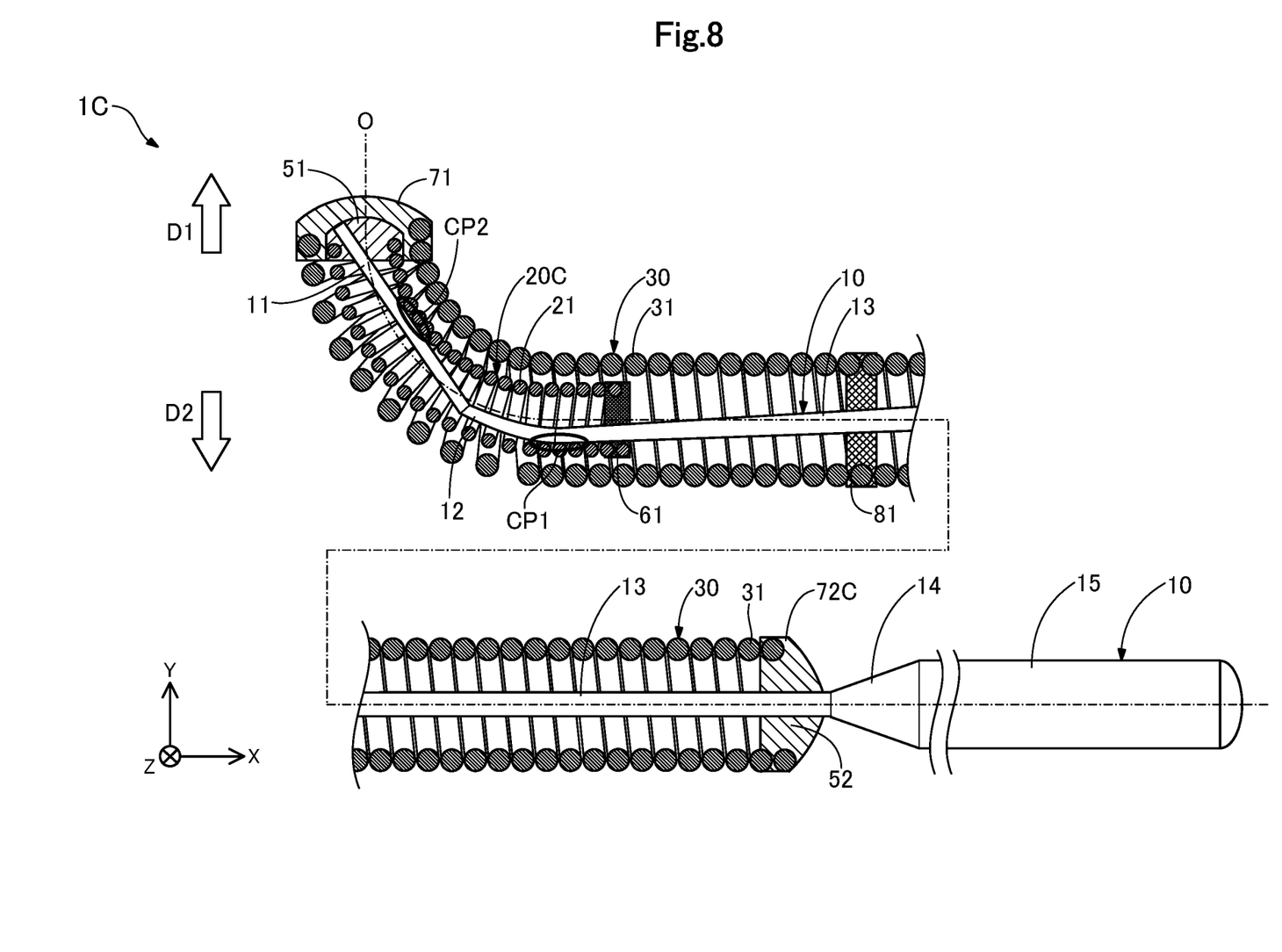
FIG. 8 is a partial cross-sectional view illustrating an overall configuration of a guide wire according to a fourth embodiment.

FIG. 8 is a partial cross-sectional view illustrating an overall configuration of a guide wire 1C according to a fourth embodiment. The guide wire 1C of the fourth embodiment has the configuration of the guide wire 1B of the third embodiment in which a coil body 20C is positioned only on the distal end side. Specifically, the coil body 20C has a length in the axis O direction (X-axis direction) shorter than that of the coil body 20 of the third embodiment. The proximal end part of the coil body 20C and the core shaft 10 are integrally held by the intermediate fixing portion 61, and thus the guide wire 1C is not provided with the proximal end side fixing portion 52. The proximal tip 72C integrally holds the proximal end part of the outer coil body 30 and the proximal end part of the core shaft 10 (the second reduced-diameter part 13).

The guide wire 1C according to the fourth embodiment can also exhibit a similar effect to the third embodiment. Further, according to the guide wire 1C of the fourth embodiment, the intermediate fixing portion 61 (first fixing portion) fixes the core shaft 10 to the proximal end part of the coil body 20C, and thus it becomes easy to form the outer coil body 30 around the coil body 20C, as illustrated in FIG. 8. Further, for example, the proximal end side of the second reduced-diameter part 13 of the core shaft 10 can be made thicker than that of the illustrated example, and the structure of each part of the guide wire 1C can be easily designed. In the illustrated example, the proximal end part of the coil body 20C and the core shaft 10 are integrally held by the intermediate fixing portion 61. However, the proximal end part of the coil body 20C and the core shaft 10 may be integrally held by an intermediate fixing portion (for example, the second intermediate fixing portion 81) other than the intermediate fixing portion 61.

Fifth Embodiment

Figure 9:
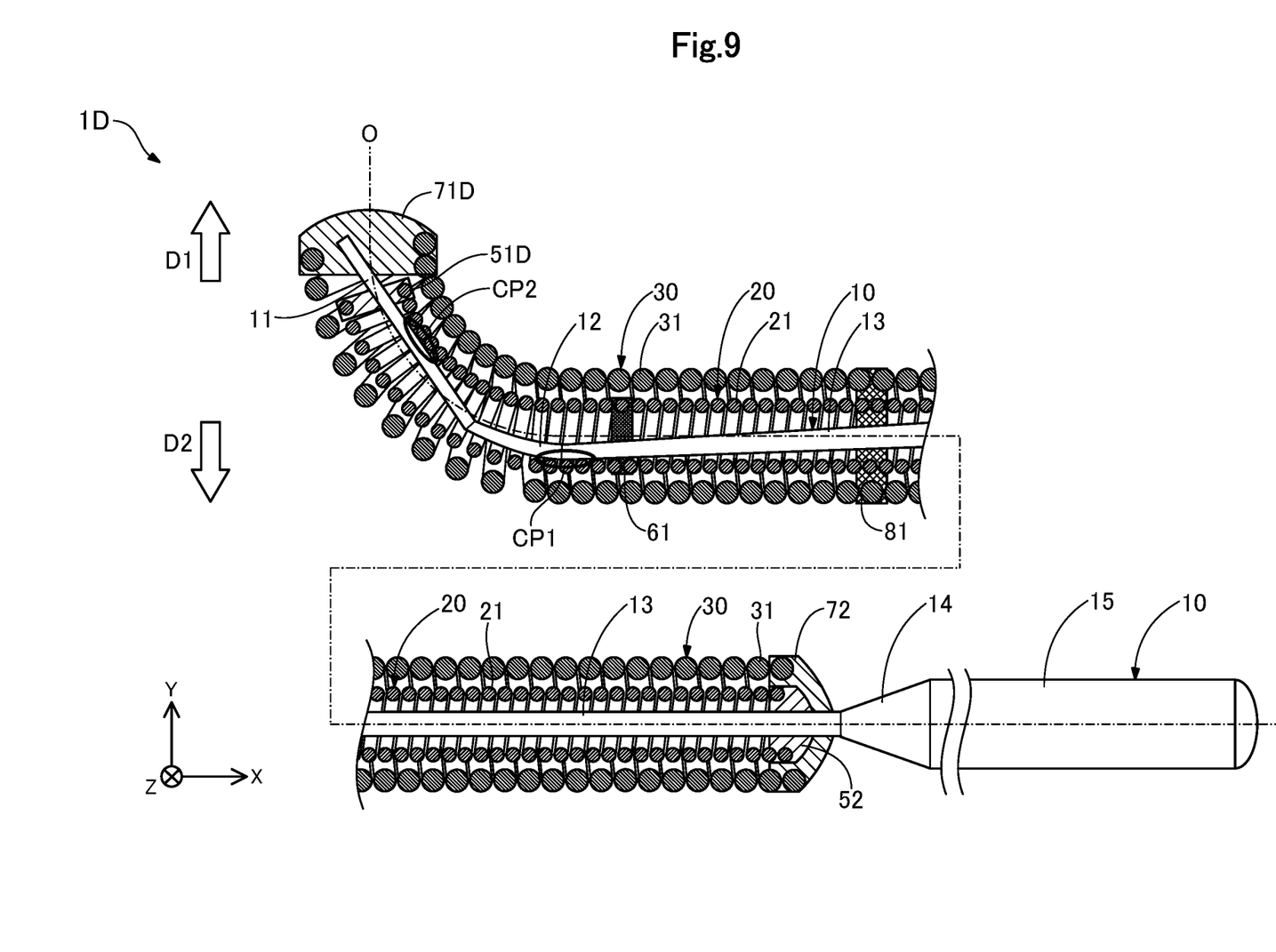
FIG. 9 is a partial cross-sectional view illustrating an overall configuration of a guide wire according to a fifth embodiment.

FIG. 9 is a partial cross-sectional view illustrating an overall configuration of a guide wire 1D according to a fifth embodiment. The guide wire 1D of the fifth embodiment has the configuration of the guide wire 1B of the third embodiment including a distal end side fixing portion 51D instead of the distal end side fixing portion 51. The distal end side fixing portion 51D integrally holds the distal end part of the coil body 20 and a portion of the small-diameter part 11 on the distal end side, instead of the distal end part of the small-diameter part 11. In addition, similarly to the distal end side fixing portion 51 of the third embodiment, the distal end side fixing portion 51D is positioned closer to the distal end of the guide wire 1D than the second contact part CP2, and functions as the second fixing portion that fixes a portion of the small-diameter part 11 arranged in a state of being inclined in the curving direction D1 in order to maintain a contact state between the core shaft 10 and the coil body 20 at the second contact part CP2. The distal tip 71D integrally holds the distal end part of the outer coil body 30 and the distal end part of the core shaft 10 (small-diameter part 11). The guide wire 1D according to the fifth embodiment can also exhibit a similar effect to the third embodiment.

Sixth Embodiment

Figure 10:
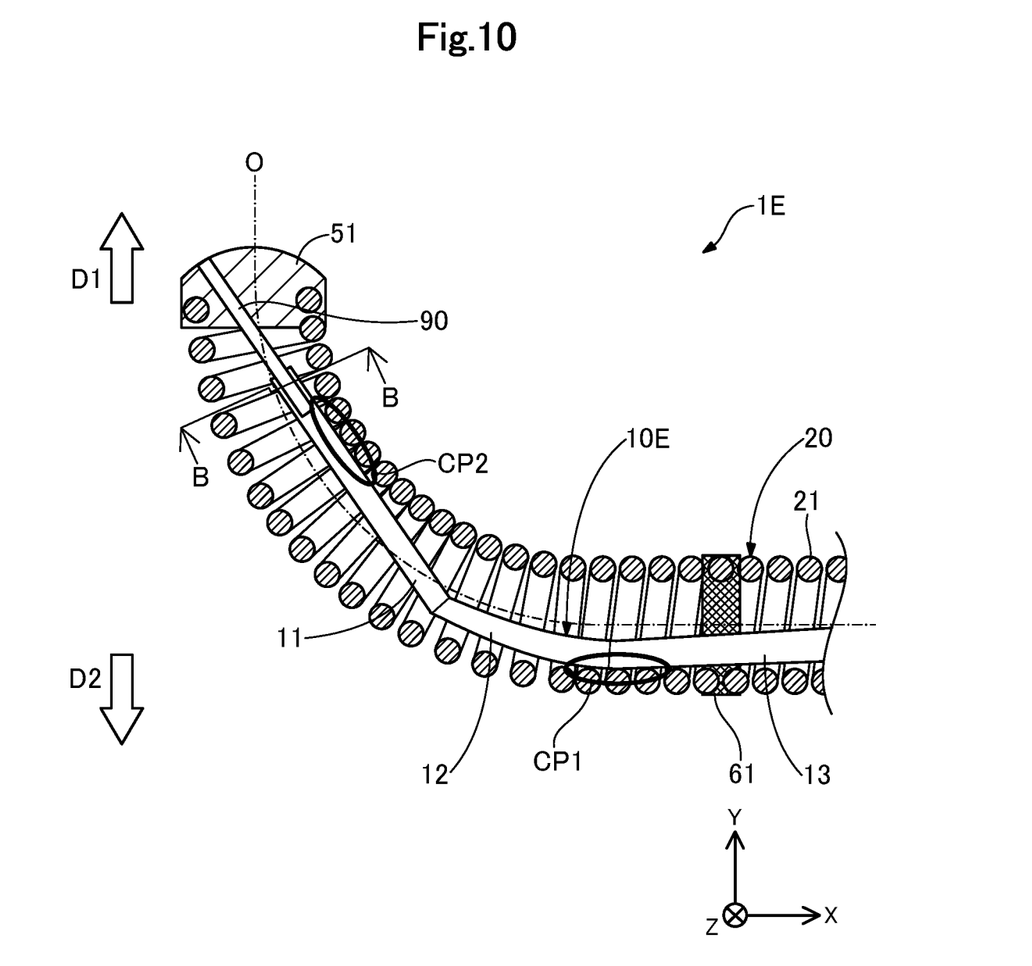
FIG. 10 is a partial cross-sectional view of a distal end side of a guide wire according to a sixth embodiment.
Figure 11:
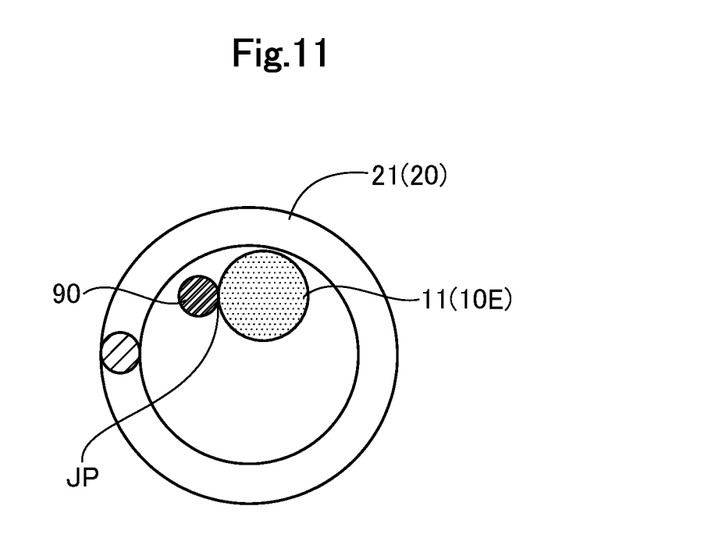
FIG. 11 is a cross-sectional view of the guide wire taken along a line B-B (FIG. 10).

FIG. 10 is a partial cross-sectional view of a distal end side of a guide wire 1E according to a sixth embodiment. FIG. 11 is a cross-sectional view of the guide wire 1E taken along a line B-B (FIG. 10). The guide wire 1E of the sixth embodiment has the configuration of the guide wire 1 of the first embodiment in which a second core shaft 90 is joined to a distal end part of a core shaft 10E. The core shaft 10E has the same configuration as the core shaft 10 except that the length of the small-diameter part 11 in the direction of the axis O is short.

The second core shaft 90 has a substantially columnar shape having a constant outer diameter. The second core shaft 90 is not curved and has a linear shape, and is arranged inside the coil body 20 and in a state of being inclined in the curving direction D1, from the proximal end side to the distal end side, similarly to the small-diameter part 11. The second core shaft 90 may be formed of the same material as the core shaft 10E or may be formed of a material different from that of the core shaft 10E. For example, if the second core shaft 90 is formed of a material having higher plastic deformability compared to the core shaft 10E, shaping at the distal end side of the guide wire 1E can be more easily performed, which is preferable. As illustrated in FIG. 11, the second core shaft 90 is joined to the small-diameter part 11 of the core shaft 10E (joint part JP). Such joining can be performed by using any bonding agent, for example, a metal solder such as silver solder, gold solder, zinc, Sn—Ag alloy, Au—Sn alloy, etc., or an adhesive such as an epoxy adhesive, etc.

The guide wire 1E according to the sixth embodiment can also exhibit a similar effect to the first embodiment. Furthermore, according to the guide wire 1E of the sixth embodiment, using the second core shaft 90 formed of a material different from that of the core shaft 10E enables changing plasticity at the distal end portion of the guide wire 1E.

Modifications of Embodiments

The disclosed embodiments are not limited to the above-described embodiments, and may be implemented in various modes without departing from the spirit and scope of the disclosed embodiments. The following modifications can be applied, for example.

[First Modification]

In the above-described first to sixth embodiments, the configurations of the guide wires 1 and 1A to 1E have been illustrated. However, the configuration of the guide wire can be variously modified. For example, the guide wires according to the above embodiments are described as a medical device used when a catheter is inserted into a blood vessel, but the guide wire may be configured to be inserted into various organs in a human body such as a lymphatic system, a biliary system, a urinary system, a respiratory system, a digestive system, a secretory gland, and reproductive organs. For example, the guide wire may not include the third reduced-diameter part and the large-diameter part, and the core shaft may be entirely covered with the coil body.

[Second Modification]

In the first to sixth embodiments, the configurations of the core shafts 10, 10A, and 10E have been illustrated. However, the configuration of the core shaft can be variously modified. For example, the small-diameter part, the first reduced-diameter part, and the second reduced-diameter part of the core shaft may not be differentiated and all of these parts may be formed as a small-diameter part having a constant outer diameter, or all of these parts may be formed as a reduced-diameter part decreasing in outer diameter from the proximal end side to the distal end side. For example, the small-diameter part, the first reduced-diameter part, and the second reduced-diameter part of the core shaft may be formed of different materials and may be joined together. For example, the cross-sectional shapes of the small-diameter part, the first reduced-diameter part, and the second reduced-diameter part of the core shaft are not limited to a substantially circular shape, and may be any shape, including a substantially rectangular shape, a substantially elliptical shape, a substantially polygonal shape, and the like. For example, a portion of the core shaft closer to the proximal end of the guide wire than the third reduced-diameter part may be formed of a plurality of core shaft members joined together. In this case, the core shaft members may be formed of the same material or different materials.

[Third Modification]

In the above-described first to sixth embodiments, examples of the configurations of the coil bodies 20 and 20C and the outer coil body 30 have been described. However, the configurations of the coil body and the outer coil body can be variously modified. For example, at least one of the coil body and the outer coil body may have a dense winding configuration having no gap between adjacent wires, a sparse winding configuration having a gap between adjacent wires, or a combined configuration of the dense winding configuration and the sparse winding configuration. At least one of the coil body and the outer coil body may include a coating resin layer made of a hydrophobic resin material, a hydrophilic resin material, or a mixture thereof, for example. For example, in at least one of the coil body and the outer coil body, the cross-sectional shape of the wire may not be substantially circular.

[Fourth Modification]

The configurations of the guide wires 1 and 1A to 1E of the first to sixth embodiments and the configurations of the guide wires of the first to third modifications may be appropriately combined. For example, the guide wire 1A of the second embodiment (the configuration including the third contact part CP3) or the guide wire 1E of the sixth embodiment (the configuration including the second core shaft 90) may be provided with the outer coil body 30 described in the third embodiment. Similarly, the guide wires 1A and 1E of the second and sixth embodiments may be provided with a coil body 20C having a short length in the direction of the axis O described in the fourth embodiment. Similarly, the guide wires 1A and 1E of the second and sixth embodiments may be provided with the distal end side fixing portion 71D described in the fifth embodiment. For example, the guide wire 1C of the fourth embodiment (the configuration including a coil body 20C having a short length in the direction of the axis O) may be provided with the distal end side fixing portion 71D described in the fifth embodiment.

Although aspects of the disclosed embodiments and modifications have been described above, the described embodiments and modifications are for facilitating understanding of various aspects of the invention, and do not limit the scope of the invention. The aspects can be modified and improved without departing from the spirit and scope of the claims, and its equivalents are included within the scope of the invention. Further, unless a technical feature is described as essential in the present specification, it may be omitted as appropriate.

DESCRIPTION OF REFERENCE NUMERALS 1, 1A to 1E . . . Guide wire
10, 10A, 10E . . . Core shaft
11, 11A . . . Small-diameter part
12 . . . First reduced-diameter part
13 . . . Second reduced-diameter part
14 . . . Third reduced-diameter part
15 . . . Large-diameter part
20, 20C . . . Coil body
21 . . . Wire
30 . . . Outer coil body
31 . . . Wire
51, 51D . . . Distal end side fixing portion
52 . . . Proximal end side fixing portion
61 . . . Intermediate fixing portion
71, 71D . . . Distal tip
72, 72C . . . Proximal tip
81 . . . Second intermediate fixing portion
90 . . . Second core shaft

What is claimed is:

1. A guide wire comprising:
a first coil body having a distal portion that is curved in a curving direction from a proximal end side of the distal portion of the first coil body to a distal end side of the distal portion of the first coil body;
a core shaft disposed within a lumen of the first coil body, the core shaft including:
a first contact part that is in direct contact with an inner surface of the first coil body on an opposite side of the guide wire that is a side of the guide wire opposite to the curving direction; and
a second contact part that is in direct contact with the inner surface of the first coil body on a side of the guide wire in the curving direction, and that is disposed at a position closer to a distal end of the guide wire than the first contact part,
a first fixing portion that fixes the core shaft to the first coil body at a position closer to a proximal end of the guide wire than the first contact part; and
a second fixing portion that fixes the core shaft to the first coil body at a position closer to the distal end of the guide wire than the second contact part.

2. The guide wire according to claim 1, wherein the second fixing portion fixes a distal end part of the core shaft to a distal end part of the first coil body.

3. The guide wire according to claim 1, further comprising:
a second coil body disposed around the first coil body, the second coil body being curved in the curving direction.

4. The guide wire according to claim 3, further comprising:
a distal tip that fixes a distal end part of the second coil body to a distal end part of the core shaft.

5. The guide wire according to claim 1, wherein the first fixing portion fixes the core shaft to a proximal end part of the first coil body.

6. The guide wire according to claim 2, further comprising:
a second coil body disposed around the first coil body, the second coil body being curved in the curving direction.

7. The guide wire according to claim 6, further comprising:
a distal tip that fixes a distal end part of the second coil body to a distal end part of the core shaft.

8. The guide wire according to claim 2, wherein the first fixing portion fixes the core shaft to a proximal end part of the first coil body.

9. The guide wire according to claim 3, wherein the first fixing portion fixes the core shaft to a proximal end part of the first coil body.

10. The guide wire according to claim 4, wherein the first fixing portion fixes the core shaft to a proximal end part of the first coil body.

11. The guide wire according to claim 1, wherein:
the first coil body comprises a coating resin layer; and
the first contact part and the second contact part are in direct contact with the coating resin layer.

12. A guide wire comprising:
a first coil body having a distal portion that is curved in a curving direction from a proximal end side of the distal portion of the first coil body to a distal end side of the distal portion of the first coil body;
a core shaft disposed within a lumen of the first coil body, wherein in the absence of external force applied to the guide wire, the core shaft includes:
a first contact part that is in direct contact with an inner surface of the first coil body on an opposite side to the curving direction of the first coil body; and
a second contact part that is in direct contact with the inner surface of the first coil body on a side of the guide wire in the curving direction, and that is disposed at a position closer to a distal end of the guide wire than the first contact part,
a first fixing portion that fixes the core shaft to the first coil body at a position closer to a proximal end of the guide wire than the first contact part; and
a second fixing portion that fixes the core shaft to the first coil body at a position closer to the distal end of the guide wire than the second contact part.

* * * * *